Figure 1:
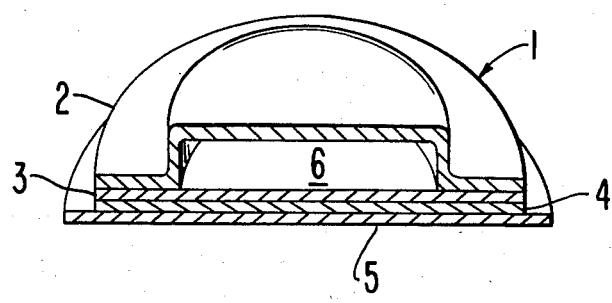

United States Patent [19]
Gale et al.

[11] Patent Number: 4,588,580
[45] Date of Patent: May 13, 1986

[54] TRANSDERMAL ADMINISTRATION OF FENTANYL AND DEVICE THEREFOR

[75] Inventors: Robert M. Gale, Los Altos; Victor Goetz, Palo Alto; Eun S. Lee, Redwood City; Lina T. Taskovich, Palo Alto; Su I. Yum, Los Altos, all of Calif.

[73] Assignee: Alza Corporation, Palo Alto, Calif.

[21] Appl. No.: 633,762

[22] Filed: Jul. 23, 1984

[51] Int. Cl.⁴ .......................... A01N 25/24; A61K 9/70
[52] U.S. Cl. ........................................... 424/21; 424/14; 424/16; 424/19; 424/22; 514/316; 514/329; 604/896; 604/897; 604/93; 604/304; 604/307
[58] Field of Search .......................... 424/14, 16, 19, 21, 424/22; 604/896, 897, 93, 94, 304, 307; 514/316, 329

[56] References Cited

U.S. PATENT DOCUMENTS

| | | | |
|---|---|---|---|
| 3,742,951 | 7/1973 | Zaffaroni | 604/304 |
| 4,060,084 | 11/1977 | Chandrasekaran et al. | 604/304 |
| 4,127,127 | 11/1978 | Wong et al. | 128/260 |
| 4,262,003 | 4/1981 | Urquhart et al. | 424/267 |
| 4,379,454 | 4/1983 | Campbell et al. | 604/897 |
| 4,379,789 | 4/1983 | Capetola et al. | 424/260 |

FOREIGN PATENT DOCUMENTS 0123117 7/1982 Japan .................................. 424/34

OTHER PUBLICATIONS

Andrews et al, "Fentanyl-A Review ", Clinics in Anaesthesiology, vol. 1, No. 1, Apr. 1983, pp. 97–122.
Isaacs, "A Safer Way to Take Your Medicine", Parade Magazine, May 12, 1985, p. 8.
Sanders, "Improved Drug Delivery", Chem and Eng News, vol. 63, No. 13, Apr. 1, 1985, pp. 30–40, 44, 45, 47 and 48.
Rensberger, "'Designer Drugs' Skirt the Law", Mar. 14, 1985, Washington Post, pp. A1, A5.

*Primary Examiner*—John Kight
*Assistant Examiner*—Nathan M. Nutter
*Attorney, Agent, or Firm*—Steven F. Stone

[57] ABSTRACT

Transdermal delivery systems for delivery of fentanyl and its analgetically effective derivatives for extended periods of time are disclosed which deliver the base form of the drug at a rate of from 0.5 to 10 μg/cm²/hr for a substantial portion of their useful life. The systems can be from 5–100 cm² in releasing surface and preferably employ an in-line amine resistant adhesive. Preferred rate controlled systems utilize an aqueous ethanolic gel to minimize drug content.

58 Claims, 8 Drawing Figures

TRANSDERMAL ADMINISTRATION OF FENTANYL AND DEVICE THEREFOR

FIELD OF INVENTION

This invention relates to the administration of fentanyl for analgetic purposes and more particularly to a method and device for administering fentanyl to a subject through intact skin over an extended period of time at a substantially constant rate.

BACKGROUND OF THE INVENTION

Fentanyl and its analgetically effective derivatives (hereafter referred to as "derivatives") such as sufentanyl, carfentanyl, lofentanyl and alfentanyl have long been known as extremely potent and effective anesthetics and analgesics. Fentanyl is described in U.S. Pat. No. 3,164,600 and its use as approved by the FDA in the United States is described in the 1984 Physician's Desk Reference, pages 1027 through 1029 with reference to the drug SUBLIMAZE® manufactured by McNeil Lab for Janssen Pharmaceutica, Inc. In use, fentanyl is normally administered as the citrate either as a bolus injection or infusion or a continuous infusion for the purposes of producing anesthesia or analgesia.

The application of transdermal drug delivery technology to the administration of a wide variety of drugs has been proposed and various systems for accomplishing this are disclosed in numerous technical journals and patents. U.S. Pat. Nos. 3,598,122, 4,144,317, 4,201,211, 4,262,003, and 4,379,454, all of which are incorporated herein by reference, are representative of various transdermal drug delivery systems of the prior art, which systems have the ability of delivering controlled amounts of drugs to patients for extended periods of time ranging in duration from several hours to several days. None of the above patents nor any other prior art of which the inventors are aware describes a transdermal delivery system which is intended to deliver fentanyl or its derivatives nor are they aware of data on skin permeability or therapeutic transdermal delivery rates adequate to design such a system. Furthermore, fentanyl and its derivatives have certain unique characteristics which impose a combination of restraints on a transdermal delivery system which have hitherto not been addressed in other systems.

Fentanyl and its derivatives are highly potent, rapidly metabolized drugs having a relatively narrow therapeutic index which produce extremely undesirable side effects on overdosage, most notably respiratory depression, which if left unchecked can cause death. They are also relatively expensive and have a high potential for abuse. We have found that these characteristics impose numerous and sometimes conflicting design constraints on a practical transdermal delivery device. For example, it would be desirable that the device deliver the drug at a substantially constant rate for at least about 24 hours while at the same time keeping the amount of drug within both the unused and depleted systems to a minimum. Another example of conflicting constraints is that the degree to which the system controls the release rate should be relatively high in order to assure that excessive amounts of the drug are not delivered in the event that the skin of a patient has been damaged or has an abnormally high permeability. But the release rate per unit area of system cannot be selected at such a low level that the onset of analgesia is delayed beyond five hours or that adequate dosages are not obtained from reasonably sized systems. In addition to these general design criteria we have discovered certain properties of fentanyl, and its derivatives such as skin permeability and drug binding in the skin which impose additional conflicting design constraints.

According to our invention we have provided methods for the transdermal delivery of fentanyl or its derivatives and transdermal delivery systems for effecting the same, which are suitable for the administration of fentanyl or its derivatives continuously through intact skin for the alleviation of pain.

It is accordingly an object of this invention to provide a method for the continuous transdermal administration of fentanyl or its derivatives.

It is another object of this invention to provide transdermal therapeutic systems usable to administer fentanyl or its derivatives at a substantially constant rate for an extended period of time to produce analgesia.

It is another object of this invention to provide rate limited, duration specified transdermal therapeutic systems for the administration of fentanyl or its derivatives to the systemic circulation.

It is another object of this invention to provide transdermal therapeutic systems for the administration of fentanyl or its derivatives in which the amount of residual drug is minimized.

It is another object of this invention to provide methods and apparatus for the transdermal administration of fentanyl or its derivatives in which the onset of analgesia occurs in a relatively short period of time.

Figure 2:
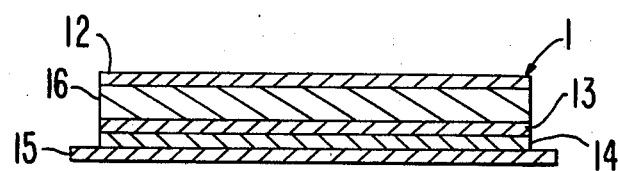
Figure 3:
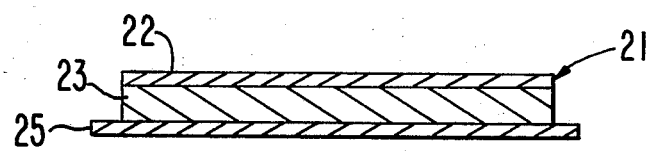
Figure 4:
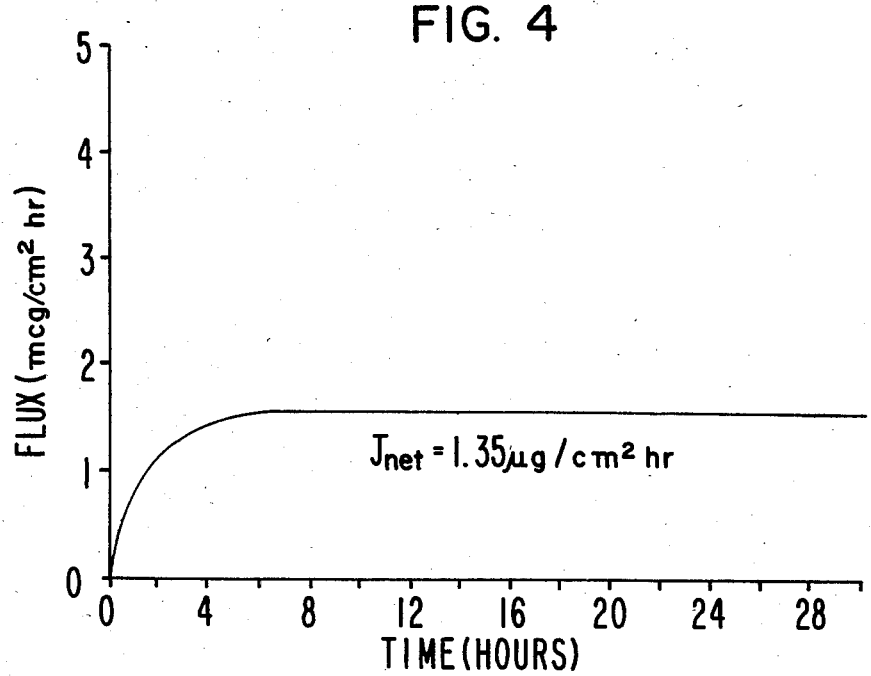
Figure 5:
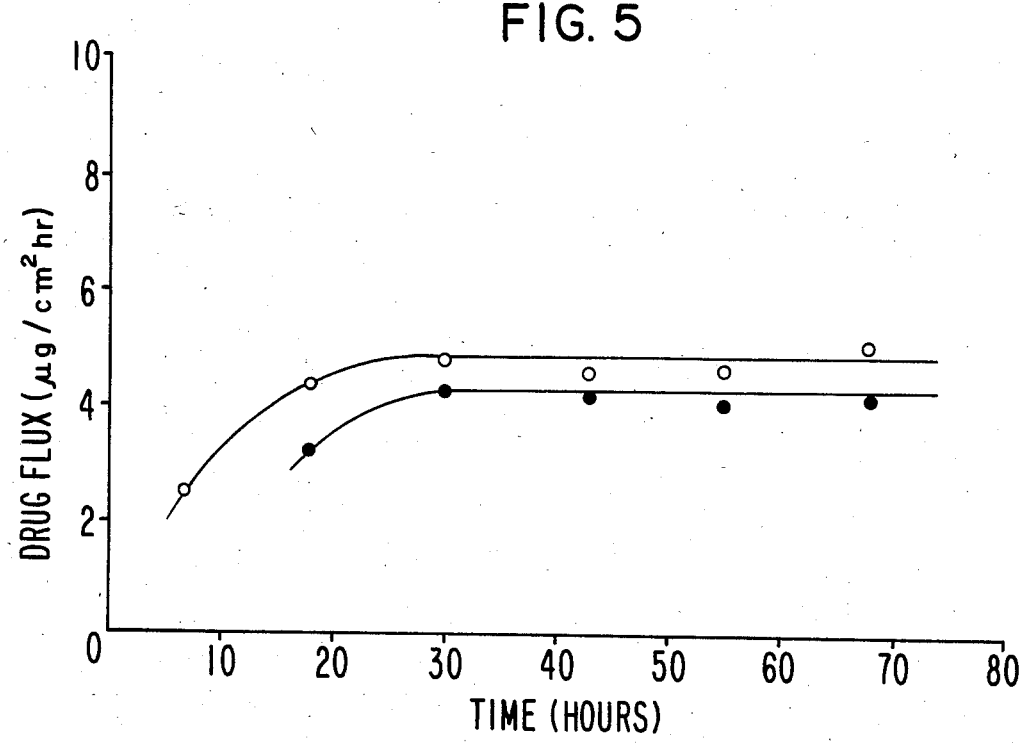
Figure 6:
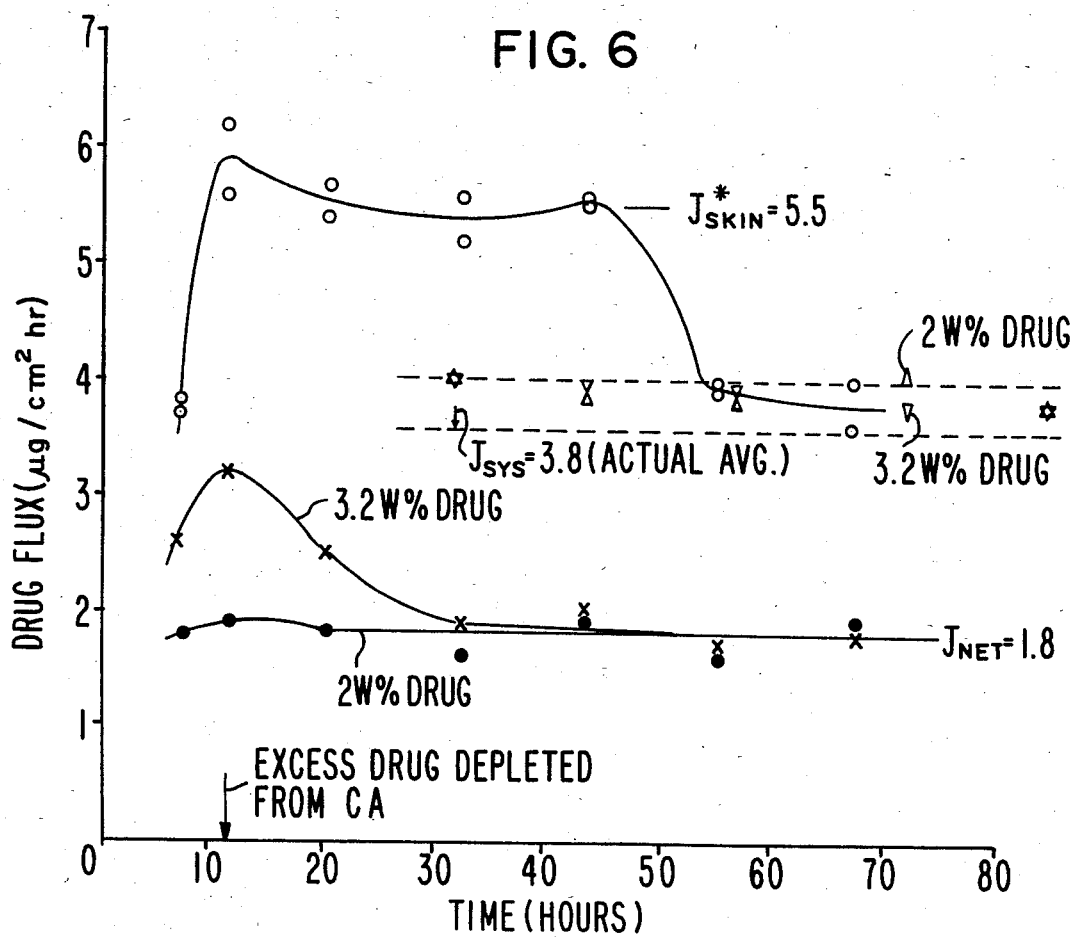
Figure 7:
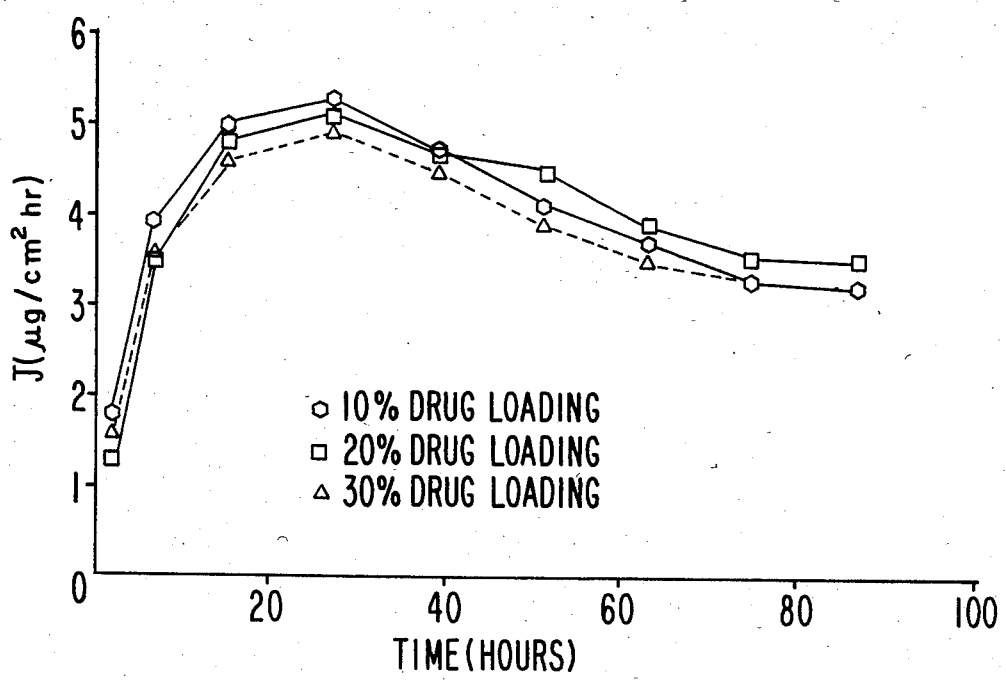
Figure 8:
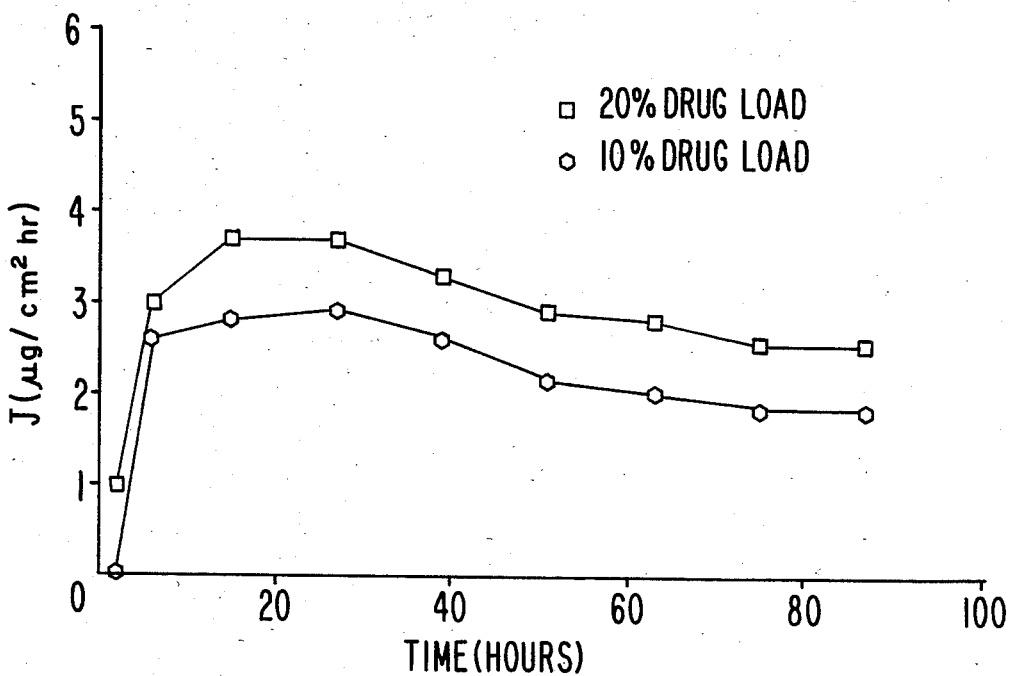

These and other objects and advantages of our invention will be readily apparent from the following description with reference to the accompanying drawings wherein:

FIG. 1 is a cross-section through a schematic, perspective view of one embodiment of transdermal therapeutic system according to this invention, prior to application to the skin, FIG. 2 is a cross-section view through another embodiment of this invention, FIG. 3 is a cross-section view through another embodiment of this invention, FIG. 4 is a plot of in vitro skin flux v time for a specific embodiment of this invention, FIG. 5 is a plot of the in vitro skin flux v time for another specific embodiment of this invention, FIG. 6 is a plot of the in vitro fluxes v time for other specific embodiments of this invention, FIG. 7 is a plot of the in vitro skin fluxes v time for other specific embodiments of this invention, and FIG. 8 is a plot of the in vitro skin fluxes v time for another specific embodiments of this invention.

DESCRIPTION OF THE INVENTION

According to our invention we have found that fentanyl or its derivatives may be administered to the human body via the transdermal route for the purpose of inducing analgesia, if administered through about 5–100 $cm^2$ and preferably about 10–50 $cm^2$ of intact skin over an extended period of time at a rate within the range of about 0.5 to 10 $\mu g/cm^2/hour$ and preferably at a rate within the range of approximately 1–5 $\mu g/cm^2/hour$. When so delivered it is possible, by appropriate selection of the surface area of the drug delivery device to obtain total drug input rates which provide an adequate range of titration for individual patient needs while maintaining a safe and effective dosage form. Steady-state administration rates obtainable according to this invention range from about 10–300 μg/hr and preferably from about 25–150 μg/hr. Administration is maintained for at least 12 hours and for up to 7 days with a 1–3 day regimen being considered preferable.

We have found that there is a relatively wide range of permeability of normal human skin to fentanyl and this permeability not only varies from individual to individual and site to site but is also highly dependent on the chemical form of the drug. We have discovered that fentanyl citrate, the form in which fentanyl is presently administered, has such a low skin permeability that it is not at all suitable for transdermal delivery even with the use of permeation enhancers. Instead we have found that, in order to obtain the delivery rates noted above, the drug should be incorporated in the transdermal therapeutic system in the form of the base. Our data indicate the permeability of normal human skin to fentanyl base is approximately 4±1.8 (S.D.) μg/cm$^2$/hr with observed extremes of 1.2 and 5.7 μg/cm$^2$/hr.

With respect to the other fentanyl derivatives noted above we believe the following relationships between relative permeability and potency to exist:

TABLE 1

| DRUG | RELATIVE POTENCY (Fentanyl = 1) |
| --- | --- |
| (1) Fentanyl | 1 |
| (2) Sufentanyl | 15 |
| (3) Carfentanyl | 34 |
| (4) Lofentanyl | 15 |
| (5) Alfentanyl | 0.25 |

Relative Skin Permeability
(1) > (2) ≧ (3) > (4) > (5)

These relationships allow for therapeutic transdermal administration of these fentanyl derivatives within the parameters set forth herein.

While our invention contemplates the delivery of fentanyl in therapeutic amounts for continuous periods from matrix type transdermal systems which rely primarily on skin permeability to control drug input rate, preferred embodiments deliver the drug from rate controlled transdermal system in which the system itself controls the maximum rate at which the drug is delivered through the skin.

The flux, Jnet, of drug delivered through the skin from a rate controlled transdermal therapeutic system is given by the following relationship:

$$\frac{1}{J_{net}} = \frac{1}{J_{skin}} + \frac{1}{J_{system}} \quad (1)$$

Thus, in order to provide a transdermal therapeutic system in which at least 50% (and preferably more) of the rate control is provided by Jsystem, the flux from the system into an infinite sink, it is necessary to substantially increase, Jskin, the flux through the skin by use of a skin permeation enhancer. Suitable permeation enhancers include without limitation ethanol and other higher alcohols, N-decylmethylsulfoxide (nDMS), polyethylene glycol monolaurate, dilaurate and related esters, glycerol mono-oleate and related mono, di and trifunctional glycerides, diethyl toluamide, A zone ® a product of Nelson Research Corp., N, N-dimethyl lauramide, N, N-dimethyl lauramine oxide, and the like, for example.

Since a conservative analysis of the existing data suggests that the permeability of normal skin to fentanyl base is in the range of about 1 to 10 μg/cm$^2$/hr with most skin being in the range of about 2–5 μg/cm$^2$/hr, sufficient permeation enhancer should preferably be provided for rate controlled systems to increase Jskin of the lowest permeability skin to a value no less than J system. Application of formula (1) clearly shows that as Jskin increases with Jsystem remaining constant, Jnet will approach that of Jsystem itself. Thus, sufficient permeation enhancer should preferably be delivered to increase the permeability of even the most impermeable skin to a value at least equal to Jsystem. This will produce a system in which at least 50% of Jnet is controlled by the system. It would be preferable if the system be at least 70% controlling and this objective can be obtained if the permeability of skin is increased to at least 2.4 times the steady state Jsystem.

When transdermal systems, according to this invention, are applied to the skin, the drug will be transferred from the system into the skin where it is absorbed into the bloodstream to produce its systemic analgetic effect. We have found that skin contains fentanyl binding sites which must be saturated before any significant absorption into the bloodstream occurs. The variation from individual to individual, and site to site appears to lie in the range of about 25–75 μg/cm$^2$ of the base formed fentanyl or its derivatives and the initial saturation of these sites should proceed rapidly in order to provide rapid onset of analgesia. Since most transdermal therapeutic systems exhibit an initial transitory, increased release of drug which occurs at a significantly higher rate than the steady-state rate later obtained, inclusion of additional amounts of the drug at the skin contacting surface of the device is not an absolute requirement. The systems described herein are capable of delivering drug at initial rates which should induce the onset of analgesia within from two to four hours after application but drug can be added to the adhesive layer or other skin contacting layer to more rapidly saturate the binding sites, if desired.

The skin binding sites are also significant in establishing an upper limit on the size of the transdermal therapeutic system and, conversely, the lower limit on the usable delivery rate. The total amount of drug contained in the binding sites is directly proportional to the surface area of the delivery system and is independent of the rate at which the drug is delivered. When a maximum sized, 100 cm$^2$ system according to this invention is employed, the total amount of drug within the binding sites could be from at least 2.5 to 7.5 mg. When such a system is removed the total amount of bound drug must be absorbed by the body before the action of the drug stops. In view of the high potency of fentanyl and its derivatives, it is preferable that the amount of drug solubilized in the skin be maintained at or below 3.75 mg level to permit prompt termination of therapy.

When continuous analgesia is desired the depleted system would be removed and a fresh system is applied to a new location. Since saturation of the skin binding sites usually occurs at substantially the same rate as absorption of bound drug, blood levels will remain substantially constant.

Having thus generally described the requirements for transdermal therapeutic systems for administering the base form of fentanyl and its derivatives and methods for their transdermal administration, the following description of various specific embodiments of the invention are provided.

Referring now to FIG. 1 a preferred embodiment of a transdermal therapeutic system 1 according to this invention comprises a pouch formed from an impermeable backing 2, a rate controlling membrane 3, and an amine resistant contact adhesive layer 4, covered by a strippable protective backing 5. The impermeable backing 2 is configured to provide a central volume which contains a drug reservoir 6 in the form of a gel having dissolved and suspended drug therein. Although preferred embodiments of this invention utilize an amine resistant in-line adhesive as shown in FIG. 1 other means for maintaining the system on the skin can be employed. Such means include a peripheral ring of adhesive outside the path of drug from the system to the skin, in which case the adhesive need not be amine resistant. The use of adhesive overlays or other fastening means such as buckles, belts, and elastic arm bands is also contemplated.

The aforementioned patents describe a wide variety of materials which can be used for fabricating the various layers of the transdermal fentanyl delivery systems according to this invention. This invention therefore contemplates the use of materials other than those specifically disclosed herein, including those which may hereafter become known to the art to be capable of performing the necessary functions.

Various drug reservoir compositions can be utilized according to this invention and include both aqueous and non-aqueous systems. A general formulation for the preferred aqueous gel system is shown in Table 2 with the gelling agent being hydroxyethyl cellulose, hydroxypropyl cellulose, hydroxypropylmethylcellulose or other known gelling agents.

TABLE 2

| GEL RESERVOIR COMPOSITION (W/W %) | | |
|---|---|---|
| Material | Broad Range | Preferred Range |
| Ethanol 95% | 0-47 | 20-35 |
| Gelling Agent | 1-10 | 1-5 |
| Base form of Drug | 0.1-10 | 0.1-2% |
| H₂O | Balance | Balance |

The water-ethanol systems described in Table 2 possess certain unique characteristics when used in combination with rate controlling membranes such as low density polyethylene (LDPE), ethylene-vinyl acetate (EVA) copolymers, (0-40% and preferably 5-18% VA) heat sealable polyesters, and elastomeric polyester block copolymers such as the HYTREL ® polymers available from DuPont and described in U.S. Pat. No. 4,127,127 which is incorporated herein by reference which exert substantial control on the fentanyl release rate without significantly effecting the ethanol release rate. This produces a dynamic situation in which the relative concentration of the ethanol in the reservoir changes with respect to the relative concentration of water and drug as the system is used. Since fentanyl and its derivatives are substantially more soluble in ethanol than water, the thermodynamic activity of the drug in the reservoir does not decrease as would normally be expected as the drug is delivered from the system. The driving force causing the drug to migrate through the rate controlling membrane is the thermodynamic activity of the drug in the solvent rather than the absolute concentration. Thus, the more rapid depletion of the ethanol causes the saturation concentration of the drug in the aqueous reservoir to decrease. By appropriate adjustment of the ethanol and drug delivery rates from the system, the activity of the drug can be maintained constant or even caused to increase during the lifetime of the system.

The rate controlling membrane can be from about 0.5-5 mils (0.0127-0.1270 mm) thick and preferably about 1-3 mils (0.25-0.076 mm) thick. To provide adequate system life, the gel loading will be from about 10-50 mg/cm² yielding a dry loading of from about 0.01-5 mg/cm².

Referring now to FIG. 2, a multilaminate type of transdermal therapeutic system according to this invention as shown. Such a transdermal therapeutic system 11 comprises a plurality of lamina bonded together into a unitary structure. The uppermost lamina 12 comprises the backing member, lamina 16 comprises a polymeric drug reservoir, lamina 13 comprises a rate controlling membrane and lamina 14 comprises an amine resistant contact adhesive. Layer 15 is a strippable backing member adapted to be removed prior to use. Elements 12, 13, 14 and 15 may be made from materials similar to those used in the corresponding elements of FIG. 1 whereas layer 16 is preferably a polymeric material, which may be plasticized and contain permeation enhancers, in which the drug is dissolved and dispersed. A typical formulation for a laminated transdermal system is shown in Table 3 the rate controlling membrane preferably being selected from the materials noted above as well as from microporous materials.

TABLE 3

| LAMINATED SYSTEM | |
|---|---|
| MATERIAL | W/W % |
| Reservoir | |
| Polyisobutylene plasticized with mineral oil (PIB/MO) or Silicone polymer | 50-95% |
| Base Form of Drug | 5-50% |
| Contact Adhesive | |
| PIB/MO, or Amine resistant silicone 0.025-0.076 mm | |

Another embodiment of this invention is shown in FIG. 3 in which the transdermal therapeutic system 21 is a simple monolith. The system 21 comprises a backing member 22 which is impermeable to the fentayl, a release liner 25 similarly impermeable and adapted to be readily removed from the drug reservoir/contact adhesive layer 23 which consists of a contact adhesive having the drug dissolved in, and if desired, dispersed therethrough. Such a system has the advantage of being easily fabricated, but in the absence of a rate controlling membrane, delivers drug at a rate which is determined primarilarily by the permeability of the skin at the site of application on the particular individual. Thus, while this system can be employed to provide drug delivery rates within the ranges described herein, the actual delivery rate cannot be as precisely controlled as would be with the systems described generally in FIGS. 1 and 2. Suitable materials for fabricating of the contact adhesive/reservoir layer include EVA polymers having approximately 0 to 18% vinylacetate content and polyisobutylene/mineral oil containing from 15 to 25% high molecular weight polyisobutelyene (an average molecular weight 1,200,000) 20 to 30% low molecular weight polyisobutelyene (average molecular weight 35,000) and balance of light mineral oil having a viscosity at 38° C. of approximately 10 centipoise. In addition to the drug, the drug reservoir-contact adhesive layer can also contain additives, permeation enhancers and other materials as are generally known to the art.

Specific examples of various transdermal therapeutic systems according to our invention which are capable of administering fentanyl at the desired rates for extended periods of time will be described in the examples set for hereinafter. However, in order for the residual drug in depleted systems to be minimized, we have discovered that the initial concentration of the fentanyl in the matrix material should be selected such that it is less than 0.5 mg/cm$^2$. For this reason the aqueous-ethanol reservoir systems which permit unit activity to be achieved at this low concentration are presently considered preferable according to our invention. In the following examples all percentages are by weight unless noted.

EXAMPLE 1

Transdermal therapeutic systems according to FIG. 1 utilizing an aqueous ethanolic gel reservoir were prepared in 10, 20 and 40 cm$^2$ sizes. Fentanyl base was added to 95% ethanol and stirred to dissolve the drug. Purified water was added to the ethanol-fentanyl solution in amounts sufficient to generate a mixture containing 14.7 mg/g of fentanyl in a 30% ethanol-water solvent. Two percent of hydroxyethyl cellulose gelling agent was added to this solution slowly with stirring and mixed until a smooth gel was obtained (approximately one hour). A 0.05 mm thick contact adhesive layer was formed on a fluorocarbon-diacrylate treated polyester film which comprised the release liner for the system by solution casting an amine resistant silicone medical adhesive onto the polyester film from a solution in trichlorotrifloroethane. A 0.05 mm thick rate controlling membrane comprised of EVA (9% VA) was pressure laminated to the exposed adhesive. A backing member comprised of a multilaminate of polyethlene, aluminum, polyester and EVA was also provided and the aqueous gel pouched between the backing member and the release liner adhesive/rate controlling membrane on a rotary heat-seal machine at a gel loading of 15 mg/cm$^2$. Sealed pouches in the sizes of 10, 20 and 40 cm$^2$ were die cut and immediately pouched to avoid loss of ethanol. The pouched systems were allowed to equilibrate for at least two weeks in order to reach equilibrium concentration of the drug and ethanol in the rate controlling and adhesive layers. After this time the drug reservoir no longer contained any excess drug and the drug concentration in the reservoir had reduced to 8.8 mg/g, the saturation concentration of fentanyl in 30% ethanol. The in vitro fentanyl flux through cadaver skin into an infinite aqueous sink at 32° C. was measured and is shown in FIG. 4. As can be seen the fentanyl flux rapidly increased to approximately 1.35 $\mu$g/cm$^2$/hr in slightly more than four hours and remained substantially constant thereafter. The saturation of the drug in skin occurred during the time the drug flux was increasing to its steady state value. After operation for approximately 24 hours substantially all of the ethanol will have been delivered and the transport rate of fentanyl through skin will have been reduced to the level obtained when no ethanol is present. It would be desirable that the use of this system be discontinued at that point. The systems originally contained approximately 200 $\mu$g/cm$^2$ of fentanyl and over the 24 hour useful life delivered approximately 50 $\mu$g/cm$^2$ resulting in a delivery of approximately 25% of the original drug loading.

EXAMPLE 2

Systems similar to those described in Example 1 were fabricated except that the drug reservoir contained 47 weight percent ethanol in water and fentanyl base at 3.2 mg/gm. The original drug gel loading was 26 mg/cm$^2$ and the control membrane was a 0.038 mm EVA film (12% VA). The in vitro transport rate through skin is shown in FIG. 5. As can be seen these systems took longer to achieve steady-state due to the original lower activity (46%) of the fentanyl but, as fentanyl activity increased due to the transport of ethanol from the system a substantially constant steady-state release of approximately 4.5 $\mu$g/cm$^2$/hr was maintained for 70 hours.

EXAMPLE 3

Systems similar to those described in Example 1 are manufactured differing from Example 1 in that the original gel concentration contains 20 weight percent ethanol with a fentanyl concentration of 8.2 mg/g and are fabricated into systems having a gel loading of 25 mg/cm$^2$. After the equilibrating period the drug concentration will fall to approximately 4.2 mg/g in the reservoir with the remainder equilibrating into the adhesive and the rate controlling membrane. After affixation to skin for approximately 24 hours the fentanyl content will have decreased to approximately 50 $\mu$g/cm$^2$. As a result of the delivery of both alcohol and fentanyl from the system, the concentration of the fentanyl in the system after approximately 72 hours will be at the saturation concentration in the then remaining aqueous solution containing no more than about 5% ethanol. At this point in time the system would be discarded and would have a residual drug content of less than 25 $\mu$g/cm$^2$. This results in a higher percentage of drug delivery than in the preceding systems.

EXAMPLE 4

A multilaminate transdermal therapeutic system of the type described with respect to FIG. 2 was prepared by adding low molecular weight polyisobutylene PIB (average molecular weight of 35,000) and high molecular weight PIB (average molecular weight 1,200,000) to a stirring vessel in a ratio of 1.25 to 1. Light mineral oil (MO) was added to the same vessel with a ratio of approximately 1.125 to 1 part of (PIB). Heptane was added and the mixture was stirred until the polymers dissolved. Sufficient fentanyl base was added to the solution to generate a blend of 20 percent fentanyl in the PIB/MO. The polymer-drug blend was solvent cast onto an occlusive backing such as described in Example 1 and allowed to evaporate to form approximate 0.05 mm thick drug reservoir. Microporous polypropelene film saturated with mineral oil was pressure laminated to the reservoir layer. A PIB/MO mixture as described above but containing sufficient additional fentanyl to provide a 2 percent loading of fentanyl as undissolved solid was cast in a layer approximately 0.05 mm thick on a siliconized polyester release liner film and the thus formed composite laminates were laminated together to form a device as shown in FIG. 3. Individual systems were die cut from this laminated film in the sizes of 2.5, 5, 10 and 20 cm circles and were packaged. The in vitro fentanyl flux from the systems produced according to this example through cadaver skin at 32° C. into an infinite sink are shown in FIG. 6. Samples differing from those described above by having a solid drug loading of 3.2 % were also fabricated. As can be seen from FIG. 6, 2% solid drug was adequate to produce a rapid onset of therapy without an unnecessarily high initial drug release rate and after the initial transitory period both systems provided a steady release rate of approximately 1.8 µg/cm²/hr for up to 70 hours.

EXAMPLE 5

A monolithic system according to FIG. 3 was fabricated by preparing a PIB/MO fentanyl base mixture as set forth in Example 4 which was solvent cast onto an occlusive backing and after evaporation of the solvent, laminated to the siliconized release liner. The PIB matrices were fabricated at 10, 20 and 30 percent fentanyl loading and drug transport rates from such systems through human cadaver skin at 32° into an infinite sink were measured. The results are shown in FIG. 7. The systems showed the typical time dependent drug release rates from a monolith however continued delivery at a relatively constant rates through skin for up to 80 hours within the ranges required according to this invention.

EXAMPLE 6

A monolithic system similar to that described in Example 5 was fabricated using Dow Corning amine resistant silicone adhesive and 20 centistoke silicone medical fluid having 10 and 20 percent fentanyl base dispersed therein. Drug permeation rates from such systems through cadaver skin into an infinite sink are shown in FIG. 8.

EXAMPLE 7

The effect of ethanol concentration on the permeability of cadaver skin to fentanyl base was investigated by measuring the in vitro drug permeation rates through cadaver skin into an infinite sink for systems containing various concentration of ethanolic gels with the results shown in Table 4.

TABLE 4

| % Ethanol | Fentanyl Skin Flux (Jnet) |
|---|---|
| 47% | 8.7 |
| 30% | 4.5 |
| 20% | 4.8 |
| 0–10% | 3.71 |

Based on these data it appears that about 40% ethanol is required to produce a significant increase in skin permeability and that at least about 20% ethanol should be employed in a rate controlled aqueous ethanol system to impart a significant degree of control of drug to the systemic circulation.

Having thus generally described our invention and described certain specific embodiments thereof including the embodiment that applicants considered to be the best mode of practicing their invention; it will be readily apparent that various modifications to the invention may be made by workers skilled in the art without departing from the scope of this invention which is limited only by the following claims wherein:

We claim:

1. A process for inducing and maintaining analgesia which comprises administering through an area of intact skin, a skin permeable form of a material selected from the group consisting of fentanyl and its analgetically effective derivatives at an analgetically effective rate and continuing the administration of said material at said rate for an extended period of time at least sufficient to induce analgesia.

2. The process for claim 1 further comprising the coadministration with said material of a skin permeation enhancer for said material.

3. The process of claim 1 wherein said extended period of time is in the range of from 12 hours to 7 days.

4. The process of claim 1 wherein the steady state administration rate of said material is maintained within the range of about 10 to 300 µg/hr for a substantial portion of said extended period of time.

5. The process of claim 1 wherein said area of intact skin is within the range of about 5 to 100 cm² and said material is delivered through the skin at a rate within the range of about 0.5 to 10 µg/cm²/hr.

6. The process of claim 5 in which said area is in the range of from about 10 to 50 cm² and said rate is in the range of about 1 to 5 µg/cm²/hr.

7. The process of claim 4 wherein the steady state

8. The process of claim 2 wherein said permeation enhancer is ethanol.

9. The process of claim 1 wherein said material is the base form of a material selected from the group consisting of fentanyl, sufentanyl, carfentanyl, lofentanyl, and alfentanyl.

10. The process of claim 2 wherein the material is fentanyl base.

11. The process of claim 3 wherein the material is fentanyl base.

12. The process of claim 4 wherein the material is fentanyl base.

13. The process of claim 5 wherein the material is fentanyl base.

14. The process of claim 6 wherein the material is fentanyl base.

15. The process of claim 7 wherein the material is fentanyl base.

16. A process for the transdermal administration of a material selected from the group consisting of fentanyl and its analgetically effective derivatives which comprises:
   (a) contacting a predetermined area of intact skin with a source of skin permeable form of said material;
   (b) maintaining said source in material transmitting relationship to said area of intact skin for an administration period of at least 12 hours; and
   (c) delivering said material into the skin at a rate within the range of about 0.1–10 µg/cm²/hour for at least about 12 hours.

17. The process of claim 16 further comprising maintaining said source at unit activity throughout said administration period.

18. The process of claim 17 wherein said predetermined area of intact skin is in the range of 5 to 100 cm².

19. The process of claim 16 wherein said material is the base form of a material selected from the group consisting of fentanyl, sufentanyl, carfentanyl, lofentanyl and alfentanyl.

20. The process of claim 18 further comprising coadministering a permeation enhancer for said material during said administration period.

21. The process of claim 16 wherein the material is fentanyl base.

22. A medical device for the transdermal administration of a material selected from the group consisting of fentanyl and its analgetically effective derivatives at an analgetically effective rate for an extended period of time of at least four hours which comprises:
(a) reservoir means containing a skin permeable form of said material in an amount sufficient to deliver said material at said analgetically effective rate for said extended period of time and,
(b) means for maintaining a said reservoir means in material transmitting relationship to intact skin.

23. The medical device of claim 22 wherein said system delivers the base form of the material through intact skin at a rate in the range of from about 10 to 300 μg/hr for a substantial portion of said period of time.

24. The medical device of claim 22 wherein said reservoir means contains a skin permeation enhancer for said material.

25. The medical device of claim 22 wherein said predetermined area is in the range of about 5-100 $cm^2$ and the rate of delivery of said material is in the range of about 0.5-10 μg/$cm^2$/hr.

26. The medical device of claim 25 wherein said area is in the range of about 10-50 $cm^2$ and said delivery rate is in the range of about 1-5 μg/$cm^2$/hr.

27. The medical device of claim 25 wherein said material is fentanyl base.

28. A medical device for continuous transdermal administration of a material selected from the group consisting of fentanyl and its analgetically effective, derivates comprising, in combination:
(a) a reservoir for said material having a skin proximal, material releasing surface area in the range of about 5-100 $cm^2$, said reservoir containing between 0.1 and 50% by weight of a skin permeable form of said material in amounts and at a concentration adequate to permit delivery of said material through intact human skin at a rate within the range of from 0.5 to 10 μg/$cm^2$/hr for at least about 12 hours and
(b) means for maintaining said reservoir in material transmitting relationship to the skin.

29. The medical device of claim 28 wherein said means for maintaining said reservoir in material transmitting relationship to the skin is an amine resistant adhesive disposed in the flow path of the material from the reservoir to the skin.

30. The medical device of claim 28 further comprising release rate controlling means disposed in the flow path of said material to the skin which means limit the flux of material from said system to a level less than the flux of material through the skin to which it is applied.

31. The medical device of claim 17 wherein said material is the base form of a material selected from the group consisting of fentanyl, sufentanyl, carfentanyl, lofentanyl and alfentanyl.

32. The medical device of claim 17 wherein said reservoir contains an aqueous gel comprising up to about 47% of 95% ethanol, 1-10% gelling agent, 0.1-10% of said material, and release rate controlling means disposed between said reservoir and the skin, said release rate controlling means being more permeable to said material than ethanol.

33. The medical device of claim 31 wherein said material is fentanyl base.

34. The medical device of claim 30 further comprising permeation enhancer means for increasing the permeability to said material of the skin to which said device is applied.

35. The medical device of claim 34 wherein said permeation enhancer means is admixed in said reservoir means.

36. The medical device system of claim 35 wherein said release rate controlling means restricts the flux of said material from said system substantially more than the flux of said permeation enhancer from said device.

37. The medical device of claim 30 wherein said reservoir is an aqueous gel comprising approximately from 0-47% of 95% ethanol., 1-10% gelling agent, 0.1-10% of said material.

38. The medical device of claim 37 wherein said aqueous gel comprises from approximately 20-35% of said ethanol, 1-5% gelling agent and 0.1-2% of said material.

39. The medical device of claim 38 wherein said release rate controlling means is substantially more permeable to ethanol than to said material.

40. The medical device of claim 39 wherein said material is initially contained in said reservoir at equilibrated levels no greater than 0.5 μg/$cm^2$.

41. The medical device of claim 39 wherein said means for maintaining said system on the skin is an amine resistant adhesive disposed on said release rate controlling means and said material is fentanyl.

42. The medical device of claim 41 wherein said surface area is in the range of from about 10-50 $cm^2$.

43. The medical device of claim 28 wherein said reservoir is an polymeric matrix having said material contained therein in an amount from about 5-50% by weight.

44. The medical device of claim 43 wherein said means for maintaining said device in material transmitting relationship to the skin comprises an amine resistant adhesive disposed in the flow path of material from the reservoir to the skin.

45. The medical device of claim 43 wherein said matrix is selected from the group consisting of polyisobutylene and silicone polymers.

46. The medical device of claim 45 wherein said device further comprises release rate controlling means disposed in the flow path of said material to the skin which limits the flux of said material from said device to a level less than the flux of material through the skin to which it is applied.

47. The medical device of claim 46 in which said means for maintaining said device in material transmitting relationship to the skin is an amine resistant adhesive disposed on said release controlling means.

48. The medical device of claim 47 wherein said material is fentanyl base.

49. The medical device of claim 28 wherein said release rate is in the range of from about 1-5 g/$cm^2$/hr and said material is fentanyl.

50. The medical device of claim 30 wherein said release rate is in the range of from about 1-5 μg/$cm^2$/hr and said material is fentanyl.

51. The medical device of claim 35 wherein said release rate is in the range of from about 1-5 μg/$cm^2$/hr and said material is fentanyl base.

52. The medical device of claim 36 wherein said release rate is in the range of from about 1-5 μg/$cm^2$/hr and said material is fentanyl.

53. The medical device of claim 38 wherein said release rate is in the range of from about 1-5 μg/$cm^2$/hr and said material is fentanyl.

54. The medical device of claim 40 wherein said release rate is in the range of from about 1-5 $\mu g/cm^2/hr$ and said material is fentanyl.

55. The medical device of claim 43 wherein said release rate is in the range of from about 1-5 $\mu g/cm^2/hr$ and said material is fentanyl.

56. The medical device of claim 44 wherein said release rate is in the range of from about 1-5 $\mu g/cm^2/hr$ and said material is fentanyl.

57. The medical device of claim 45 wherein said release rate is in the range of from about 1-5 $\mu g/cm^2/hr$ and said material is fentanyl.

58. The medical device of claim 47 wherein said release rate is in the range of from about 1-5 $\mu g/cm^2/hr$ and said material is fentanyl.

* * * * *

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

It is certified that error appears in the above-identified patent and that said Letters Patent is hereby corrected as shown below:

In the REEXAMINATION CERTIFICATE, page 2, first column, in the citation, "The Dawn of Transdermal Man", "Cyrus" should read --Cygnus--. Page 2, second column to page 3, first column, delete "C. Prottey, "The Molecular...(1985), pp. 57-60.". Page 3, after the citation of AIChE Journal, Volume 21, Number 5, Pages 985-996, insert --J.D. Borel, Contemp. Anaesth. Pract., Vol. 7, pp. 1-18 (1983).
P.A.J. Janssen, Acta. Anaesth. Scand., Vol. 26, pp. 262-268 (1982).
Y.W. Chien, "Transdermal Controlled-Release Drug Administration", in Novel Drug Delivery Systems, New York, Marcel Dekker, Inc. (1982).
R.M.B. Wright et al, Lancet, November 8, 1980, p. 1033.
D.A. McClain et al, Clin. Pharmacol. & Therapeutics, Vol. 28, No. 6 (1980).
W.D. White et al, Br. Medical Journal, Vol. 21, p. 166, (1979).
R. Schleimer et al, Clin. Pharmacol. Therapeutics, Vol 23, pp. 188-194, (1978).--.

Column 1, line 16, insert --Column 1, lines 17-25:
Fentanyl and its analgetically effective derivatives (hereafter referred to as "derivatives") such as [sufentanyl] *sufentanil*, [carfentanyl] *carfentanil*, [lofentanyl] *lofentanil*, and [alfentanyl] *alfentanil* have long been known as extremely potent and effective anesthetics and analgesics. Fentanyl is described in U.S. Pat. No. 3,164,600 and its use as approved by the FDA in the United States is described in the 1984 Physician's Desk Reference, pages 1027 through 1029 with reference to the drug SUBLIMAZE\ manufactured by McNeil Lab for Janssen Pharmaceuticals, Inc. In use fentanyl is normally administered as the citrate either as a bolus injection or infusion or a continuous infusion for the purpose of producing anesthesia or analgesia.

UNITED STATES PATENT AND TRADEMARK OFFICE
CERTIFICATE OF CORRECTION

PATENT NO. : B1 4,588,580
DATED : January 3, 1989
INVENTOR(S) : Robert M. Gale, et al.

It is certified that error appears in the above-identified patent and that said Letters Patent is hereby corrected as shown below:

Column 3 lines 23-33:

TABLE 1

| Drug | Relative Potency (Fentanyl = 1) |
|---|---|
| (1) Fentanyl | 1 |
| (2) [Sufentanyl] *sufentanil* | 15 |
| (3) [Carfentanyl] *carfentanil* | 34 |
| (4) [Lofentanyl] *lofentanil* | 15 |
| (5) [Alfentanyl] *alfentanil* | 0.25 |

Relative Skin Permeability
(1) > (2) ≥ (3) > (4) > (5)

While our invention contemplates the delivery of fentanyl in therapeutic amounts for continuous periods from matrix type transdermal systems which rely primarily on skin permeability to control drug rate, preferred embodiments deliver the drug from rate controlled transdermal systems in which the system itself controls the maximum rate at which the drug is delivered through the skin---. Column 2, line 31, "(9VA)" should read --(9% VA)--; line 38, "49" should read --40--. Column 3, line 4, "[a]" should read --vessel in a--; line 14, "0.05 mm thick" should read --0.05 mm thick--; lines 15-18, "*film saturated with...to provide a*" should read -- film saturated with mineral oil was pressure laminated to the reservoir layer. A PIB/MO mixture as described above but containing sufficient additional fentanyl to provide a---. Column 5, line 10, "cm$^2$/hr" should read --cm$^2$/hr--; line 21,

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

Page 3 of 11

It is certified that error appears in the above-identified patent and that said Letters Patent is hereby corrected as shown below:

delete "said administration period". Column 6, line 9, "fentyl" should read --fentanyl--, line 19 after "[human]" insert --skin--. Column 7 line 17, "said re-" should read --said [re- --. Column 8 after Claim 60 insert the following claims 61-110:

--61. The device of claim 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 or 58 wherein said device delivers said material at said analgetically effective administration rate for at least about 3 days.

62. A medical device for inducing and maintaining analgesia in a human being by the continuous, transdermal administration of fentanyl and its analgetically effective derivatives to a human being at analgetically effective rates throughout a predetermined analgetically effective administration period comprising, in combination:

a) a drug reservoir comprising said material distributed within a composition comprising a solution of a vehicle and a skin permeation enhancer for said material, said material being less soluble in said vehicle than in said permeation enhancer, said material being present in said reservoir in an amount in excess of the amount of said material that will be administered throughout said administration period;

b) release rate controlling means disposed in the flow path of said material to the skin, which means limit the flux of material from said system to a level less than the enhanced flux of the material through the skin, said release rate controlling means being less permeable to the vehicle than to the permeation enhancer; and c) means for maintaining said reservoir in material and permeation enhancer transmitting relationship to an area of the skin of said human being; whereby the solubility of the

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

It is certified that error appears in the above-identified patent and that said Letters Patent is hereby corrected as shown below:

material in the drug reservoir will decrease as the material and the permeation enhancer are delivered from the device and the amount of drug required to maintain unit activity in the reservoir may be reduced.

63. The device of claim 62 wherein said material is fentanyl, said vehicle is water and said permeation enhancer is ethanol.

64. The device of claim 62 or 63 wherein the initial equilibrated concentration of said material in said reservoir is no greater than about 2% by weight.

65. The device of claim 62 or 63 wherein said administration period is at least about 3 days.

66. The device of claim 64 wherein said administration period is at least about 3 days.

67. A process for inducing and maintaining analgesia in a human being by the transdermal administration of a material selected from the group consisting of fentanyl and its analgetically effective derivatives to a human being at analgetically affective rates during an analgetically effective administration period, which comprises:

a) placing a reservoir comprising a mixture of said material in a composition comprising a solution of a vehicle and a skin permeation enhancer for said material, said material being more soluble in said permeation enhancer than in said vehicle and being present in said composition in an amount in excess of the amount that will be delivered during said administration period, in material and permeation enhancer transmitting relationship to an area of intact skin on said human being;

b) maintaining said reservoir in material and permeation enhancer transmitting relationship to an area of intact skin on said human being throughout said administration period;

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

It is certified that error appears in the above-identified patent and that said Letters Patent is hereby corrected as shown below:

c) restricting the release of said material to the skin to a flux lower than the flux of said material through the skin in the presence of said permeation enhancer; and d) decreasing the solubility of said material in said reservoir composition throughout said administration period;

whereby the amount of said material required to maintain unit activity in said reservoir may be reduced.

68. The process of claim 67 wherein said vehicle is water and said permeation enhancer is ethanol.

69. The process of claim 68 wherein said material is fentanyl.

70. The process of claim 67, 68 or 69 wherein said administration period is at least about 3 days.

71. A medical device for inducing and maintaining analgesia in a human being by the transdermal administration of fentanyl to a human being through a predetermined area of intact skin at an analgetically effective rate during an analgetically effective extended period of time of at least about 24 hours which comprises:

a) fentanyl reservoir means including a reservoir composition containing fentanyl in an amount sufficient to deliver fentanyl at said analgetically effective rate for said extended period of time, said reservoir composition comprising an aqueous composition containing about 20 - 35% ethanol on a 95% ethanol basis and 0.1 - 2% fentanyl;

b) release rate controlling means disposed in the path of migration of said ethanol and fentanyl from said reservoir to the skin, said rate controlling means being less permeable to water than to ethanol and being more permeable to ethanol than fentanyl, said release rate controlling means limiting the flux of fentanyl from said system to a value less than the flux of

UNITED STATES PATENT AND TRADEMARK OFFICE
CERTIFICATE OF CORRECTION

PATENT NO. : B1 4,588,580
DATED : January 3, 1989
INVENTOR(S) : Robert M. Gale, et al.

It is certified that error appears in the above-identified patent and that said Letters Patent is hereby corrected as shown below:

fentanyl through the skin in the presence of said permeation enhancer; and c) means for maintaining said reservoir means in fentanyl and ethanol transmitting relationship to the intact skin on said human being.

72. The device of claim 71 wherein said reservoir composition is an aqueous gel and further comprises about 1-5% of a gelling agent.

73. The device of claim 71 wherein said rate controlling means comprises a material selected from the group consisting of low density polyethylene and ethylene-vinyl acetate copolymers having a vinyl acetate content of up to about 40%.

74. The device of claim 72 wherein said rate controlling means comprises a material selected from the group consisting of low density polyethylene and ethylene-vinyl acetate copolymers having a vinyl acetate content of up to about 40%.

75. The device of claim 71 or 72 wherein said rate controlling means comprises an ethylene-vinyl acetate copolymer containing about 9% vinyl acetate.

76. The device of claim 71 or 72 wherein said rate controlling means comprises an ethylene-vinyl acetate copolymer containing about 12% vinyl acetate.

77. The device of claim 71, 72, 73 or 74 wherein said extended period of time is about 3 days.

78. A medical device for inducing and maintaining analgesia in a human being by the transdermal administration of fentanyl base to a human being through a predetermined area of intact skin at an analgetically effective rate during an analgetically effective extended period of time which comprises:

a) fentanyl reservoir means including a reservoir composition containing fentanyl in an amount sufficient to deliver

UNITED STATES PATENT AND TRADEMARK OFFICE
CERTIFICATE OF CORRECTION

PATENT NO. : B1 4,588,580
DATED : January 3, 1989
INVENTOR(S) : Robert M. Gale, et al.

It is certified that error appears in the above-identified patent and that said Letters Patent is hereby corrected as shown below:

fentanyl at said analgetically effective rate for said extended period of time, said reservoir composition comprising an aqueous gel containing about 20 - 35% ethanol on a 95% ethanol basis and 0.1 - 2% fentanyl, and about 1 - 5% of a gelling agent, said gel being present in said reservoir at a loading of 10 - 50 mg/cm$^2$;

b)    release rate controlling means for limiting the flux of fentanyl from said device to a level below that of the enhanced flux of fentanyl through the skin disposed in the path of migration of said ethanol and fentanyl from said reservoir to the skin, said rate controlling means being less permeable to water than to ethanol and being more permeable to ethanol than fentanyl; and c)    means for maintaining said reservoir means in fentanyl and ethanol transmitting relationship to the intact skin on said human being.

79.    The device of claim 78 wherein said analgetically effective rate is in the range of about 10-300 µg/hr.

80.    The device of claim 78 wherein said analgetically effective rate is in the range of about 25 - 150 µg/hr.

81.    The device of claim 78, 79 or 80 wherein said rate controlling means is an ethylene-vinyl acetate copolymer having a vinyl acetate content in the range of about 9 - 12%.

82.    The process of claim 1, 2, 3, 4, 5, 6, 7, 8, 9, 10, 11, 12, 13, 14, 15, 16, 17, 18, 19, 20, 21, 67, 68, 69, 100 or 105 wherein the administration rate declines during the administration period.

83.    The process of claim 82 wherein said administration period is at least about 3 days.

84.    The device of claim 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56 57, 58, 62, 63, 71, 72,

UNITED STATES PATENT AND TRADEMARK OFFICE
CERTIFICATE OF CORRECTION

PATENT NO. : B1 4,588,580
DATED : January 3, 1989
INVENTOR(S) : Robert M. Gale, et al.

It is certified that error appears in the above-identified patent and that said Letters Patent is hereby corrected as shown below:

73, 74, 101 or 106 wherein the rate of administration declines during the administration period.

85. The device of claim 66 wherein the rate of administration declines during the administration period.

86. The device of claim 78 wherein the rate of administration declines during the administration period.

87. The device of claim 84 wherein the administration period is at least about 3 days.

88. The device of claim 71, 72, 73, 74, 78, 79 or 80 wherein the initial equilibrated fentanyl loading in said device does not exceed about 0.5 mg/cm$^2$.

89. The process of claim 1, 2, 3, 4, 5, 6, 7, 8, 16, 17, 18, 20, 67, 68, 100 or 105 wherein said material is sufentanil.

90. The process of claim 1, 2, 3, 4, 5, 6, 7, 8, 16, 17, 18, 20, 67, 68, 100 or 105 wherein said material is carfentanil.

91. The process of claim 1, 2, 3, 4, 5, 6, 7, 8, 16, 17, 18, 20, 67, 68, 100 or 105 wherein said material is lofentanil.

92. The process of claim 1, 2, 3, 4, 5, 6, 7, 8, 16, 17, 18, 20, 67, 68, 100 or 105 wherein said material is alfentanil.

93. The device of claim 22, 23, 24, 25, 26, 28, 29, 30, 32, 34, 35, 36, 37, 38, 39, 40, 43, 44, 45, 46, 47, 62, 101 or 106 wherein said material is carfentanil.

94. The device of claim 22, 23, 24, 25, 26, 28, 29, 30, 32, 34, 35, 36, 37, 38, 39, 40, 43, 44, 45, 46, 47, 62, 101 or 106 wherein said material is lofentanil.

95. The device of claim 22, 23, 24, 25, 26, 28, 29, 30, 32, 34, 35, 36, 37, 38, 39, 40, 43, 44, 45, 46, 47, 62, 101 or 106 wherein said material is alfentanil.

96. The device of claim 22, 23, 24, 25, 26, 28, 29, 30, 32, 34, 35, 36, 37, 38, 39, 40, 43, 44, 45, 46, 47, 62, 101 or 106 wherein said material is sufentanil.

UNITED STATES PATENT AND TRADEMARK OFFICE
CERTIFICATE OF CORRECTION

PATENT NO. : B1 4,588,580
DATED : January 3, 1989
INVENTOR(S) : Robert M. Gale, et al.

It is certified that error appears in the above-identified patent and that said Letters Patent is hereby corrected as shown below:

97. The process of claim 1, 2, 4, 5, 6, 7, 8,, 9, 10, 12, 13, 14, 15, 100 or 105 wherein said extended period of time is at least about 24 hours.

98. The process of claim 67, 68 and 69 wherein said administration period is at least about 24 hours.

99. The device of claim 78, 79 or 80 wherein said extended period of time is at least about 24 hours.

100. A process for inducing and maintaining analgesia in a human being by the transdermal administration of a material selected from the group consisting of fentanyl and its analgetically effective derivatives which comprises transdermally administering to said human being through an area of intact skin of no greater than about 100 $cm^2$, a skin permeable form of said material at an analgetically effective rate and continuing the administration of said material to said human being at said rate for an extended period of time at least sufficient to induce analgesia.

101. A medical device for inducing and maintaining analgesia in a human being by the transdermal administration to a human being of a material selected from the group consisting of fentanyl and its analgetically effective derivatives at an analgetically effective rate for an extended period of time of at least about 24 hours and sufficient to induce and maintain analgesia which comprises:

a) reservoir means containing a skin permeable form of said material in an amount sufficient to deliver said material at said analgetically effective rate for said extended period of time; and b) means for maintaining said reservoir means in material transmitting relationship to a predetermined area of intact skin on said human being of no greater than about 100 $cm^2$.

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

It is certified that error appears in the above-identified patent and that said Letters Patent is hereby corrected as shown below:

102. The process of claim 67, 68 or 69 wherein said area of intact skin is no greater than about 100 $cm^2$.

103. The process of claim 70 wherein said area of intact skin is no greater than about 100 $cm^2$.

104. The device of claim 23, 62, 63, 71, 72, 73, 74, 78, 79, 80 or 86 wherein said area of skin is no greater than about 100 $cm^2$.

105. A process for inducing and maintaining analgesia in a human being by the transdermal administration of a material selected from the group consisting of fentanyl and its analgetically effective derivatives which comprises transdermally administering to said human being through an area of intact skin of no greater than about 50 $cm^2$, a skin permeable form of said material at an analgetically effective rate and continuing the administration of said material to said human being at said rate for an extended period of time at least sufficient to induce analgesia.

106. A medical device for inducing and maintaining analgesia in a human being by the transdermal administration to a human being of a material selected from the group consisting of fentanyl and its analgetically effective derivatives at an analgetically effective rate for an extended period of time of at least about 24 hours and sufficient to induce and maintain analgesia which comprises:

a) reservoir means containing a skin permeable form of said material in an amount sufficient to deliver said material at said analgetically effective rate for said extended period of time; and b) means for maintaining said reservoir means in material transmitting relationship to a predetermined area of intact skin on said human being of no greater than about 50 $cm^2$.

UNITED STATES PATENT AND TRADEMARK OFFICE
CERTIFICATE OF CORRECTION

PATENT NO. : B1 4,588,580

DATED : January 3, 1989

INVENTOR(S) : Robert M. Gale, et al.

It is certified that error appears in the above-identified patent and that said Letters Patent is hereby corrected as shown below:

107. The process of claim 67, 68 or 69 wherein said area of intact skin is no greater than about 50 $cm^2$.

108. The process of claim 70 wherein said area of intact skin is no greater than about 50 $cm^2$.

109. The device of claim 23, 62, 63, 71, 72, 73, 74, 78, 79, 80 or 86 wherein said area of skin is no greater than about 50 $cm^2$.

110. The device of claim 23 or 79 wherein said rate is in the range of from 25 - 150 µg/hr.--.

Signed and Sealed this

Twenty-second Day of August, 1989

Attest:

DONALD J. QUIGG

Attesting Officer

Commissioner of Patents and Trademarks

REEXAMINATION CERTIFICATE (986th)

United States Patent [19]

Gale et al.

[11] B1 4,588,580

[45] Certificate Issued  Jan. 3, 1989

[54] TRANSDERMAL ADMINISTRATION OF FENTANYL AND DEVICE THEREFOR

[75] Inventors: Robert M. Gale, Los Altos; Victor Goetz, Palo Alto; Eun S. Lee, Redwood City; Lina T. Taskovich, Palo Alto; Su I. Yum, Los Altos, all of Calif.

[73] Assignee: Alza Corporation, Palo Alto, Calif.

Reexamination Request
No. 90/001,245, May 26, 1987
No. 90/001,271, Jul. 6, 1987

Reexamination Certificate for:
Patent No.: 4,588,580
Issued: May 13, 1986
Appl. No.: 633,762
Filed: Jul. 23, 1984

[51] Int. Cl.⁴ .................. A01N-25/24; A61K 9/70
[52] U.S. Cl. ........................... 424/21; 424/14; 424/16; 424/19; 424/22; 514/316; 514/329; 604/896; 604/897; 604/93; 604/304; 604/307
[58] Field of Search .............. 424/14, 16, 19, 21, 424/22; 604/896, 897, 93, 94, 304, 307; 514/316, 329

[56] References Cited

U.S. PATENT DOCUMENTS

| | | | |
|---|---|---|---|
| 3,053,255 | 9/1962 | Meyer | 128/268 |
| 3,598,123 | 8/1971 | Zaffaroni | 128/268 |
| 3,734,097 | 5/1973 | Zaffaroni | 128/268 |
| 3,742,951 | 8/1971 | Zaffaroni | 128/268 |
| 3,797,494 | 3/1974 | Zaffaroni | 128/268 |
| 3,797,494 | 3/1974 | Zaffaroni | 128/268 |
| 3,854,480 | 12/1974 | Zaffaroni | 128/260 |
| 3,896,238 | 7/1975 | Smith | 424/358 |
| 3,903,256 | 9/1975 | MacMillan et al. | 424/59 |
| 3,964,482 | 6/1976 | Gerstel et al. | 128/260 |
| 3,972,995 | 8/1976 | Tsuk et al. | 424/28 |
| 3,993,072 | 11/1976 | Zaffaroni | 128/260 |
| 3,996,934 | 12/1976 | Zaffaroni | 128/268 |
| 4,006,218 | 2/1977 | Sipos | 424/54 |
| 4,031,894 | 6/1977 | Urquhart et al. | 128/268 |
| 4,130,643 | 12/1978 | Smith | 424/238 |
| 4,201,211 | 5/1980 | Chandresekaran et al. | 128/268 |
| 4,262,003 | 4/1981 | Urquhart et al. | 424/267 |
| 4,286,592 | 9/1981 | Chandresekaran et al. | 128/260 |
| 4,306,551 | 12/1981 | Hymes et al. | 128/156 |
| 4,314,557 | 2/1982 | Chandreseakaran et al. | 128/260 |
| 4,316,893 | 2/2319 | Rajadyaksha | 424/180 |
| 4,379,454 | 4/1983 | Campbell | 604/897 |
| 4,486,423 | 12/1984 | Kenyhercz | 424/267 |
| 4,655,767 | 4/1987 | Woodard et al. | 604/896 |

FOREIGN PATENT DOCUMENTS

| | | |
|---|---|---|
| 82498 | 6/1988 | Australia . |
| 56100716 | 12/1981 | Japan . |
| 2093694 | 9/1922 | United Kingdom . |
| 1577259 | 10/1980 | United Kingdom . |
| 2081582 | 2/1982 | United Kingdom . |
| 2095108 | 9/1982 | United Kingdom . |
| 2100605 | 1/1983 | United Kingdom . |

OTHER PUBLICATIONS

R. Cargill, et al., "Systemic Delivery of Timolol After Dermal Application: Transdermal Flux and Skin Irritation Potential in the Rat and Dog", Pharmaceutical Research, vol. 3, No. 4 (1986).

Goodman and Gilman's The Pharmacological Basis of Therapeutics, Seventh Edition, MacMillan Publishing Company, New York (1985), pp. 3-34 and 130-131.

C. J. H. Andrews, et al., "Fentanyl—A Review", Clinics in Anaesthesiology, vol. 1, No. 1 (Apr. 1983).

John G. Wagner, Fundamentals of Clinical Pharmacokinetics, First Edition, pp. VII-XIII, 1-52, 57-59, 82, 90-120 and 307-336.

C. H. Nightingale, et al., "Basic Principles of Pharmacokinetics", Clinics in Laboratory Medicine, vol. 7, No. 2 (Jun. 1987).

W. S. Nimmo, et al., "Fentanyl by Constant Rate I.V. Infusion for Postoperative Analgesia", Br. J. Anaesth., vol. 57 (1985), pp. 250-254.

D. J. R. Duthie, et al., "The Pharmacokinetics of Fentanyl by Constant Rate I.V. Infusion for Pain Relief After Surgery", Anesthesiology, vol. 63, No. 3A (Sep. 1985), p. A282.

D. J. R. Duthie, et al., "Pharmacokinetics of Fentanyl During Constant Rate I.V. Infusions for the Relief of Pain After Surgery", Br. J. Anaesth., vol. 58, (1986), pp. 950-956.

W. S. Nimmo, et al., "Plasma Fentanyl Concentrations After Transdermal or I.V. Infusion of Fentanyl", Anesthesiology, vol. 65 (3A) (Sep. 1986).

G. K. Gourlay, et al., "An Evaluation of the Pharmacokinetics and Efficacy of Transdermal Fentanyl in the Treatment of Postoperative Pain", International Congress of Pain, Hamburg, Germany (Aug. 1987).

F. O. Holley, et al., "Continuous Delivery of Fentanyl and Postoperative Analgesia", Drug Delivery Technologies, p. 83.

F. O. Holley, et al., "Transdermal Administration of Fentanyl for Post-operative Analgesia", Anesthesiology, vol. 65 (3A) (Sep. 1986), p. A548.

R. A. Caplan, et al., "Transdermal Delivery of Fentanyl for Postoperative Pain Control".

R. V. Oden, et al., "Effect on Ventilation of Transdermal Fentanyl Compared to Intramuscular Morphine (List continued on next page.)

Primary Examiner—John Kight, III
Assistant Examiner—Nathan M. Nutter

[57] ABSTRACT

Transdermal delivery systems for delivery of fentanyl and its analgetically effective derivatives for extended periods of time are disclosed which deliver the base form of the drug at a rate of from 0.5 to 10 $\mu g/cm^2/hr$ for a substantial portion of their useful life. The systems can be from 5-100 $cm^2$ in releasing surface and preferably employ an in-line amine resistant adhesive. Preferred rate controlled systems utilize an aqueous ethanolic gel to minimize drug content.

OTHER PUBLICATIONS for Postoperative Analgesia Following Upper Extremity Orthopedic Surgery", Pain Supplement 4 (1987), p. S156.

P. M. Plezia, et al., "Transdermal Therapeutic System (Fentanyl) for Postoperative Pain: An Efficacy, Toxicity, and Pharmacokinetic Trial", Anesthesiology, vol. 66, No. 3A (Sep. 1986) p. A210.

P. K. Narang, et al., "Disposition of Fentanyl (F) in Cancer Patients".

R. Prather, et al., "Pharmacokinetics of Transdermal (TTS) Fentanyl in Surgical Patients", Pharm. Res. 4(2), Suppl., 1987, p. PP-700.

Report of the Task Group on Reference Man, International Commission on Radiological Protection, No. 23, Adopted Oct. 1984, Pergamon Press, pp. 8–23.

E. Redd, "Cancer Pain Under Development", Oncology Times, (Jul. 1, 1987), pp. 5 and 33.

G. L. Flynn, et al., "Physicochemical Aspects of Drug Delivery to and Via the Skin", Topics in Pharmaceutical Sciences 1985, Elsevier Science Publishers, (1985) pp. 313–328.

S. D. Roy, et al., "Concepts in Transdermal Delivery of Narcotics I: Enzymatic Activity in Hairless Mouse Skin and Human Epidural Homogenates", #59 and "Concepts in Transdermal Delivery of Narcotics II: In Vitro Permeation of Sufentanil and Fentanyl Through Human Skin", #60, Pharmaceutical Research, vol. 3, No. 5, Plenum Press (1985) p. 54S.

E. A. Welchew, et al., "Continuous Thoracic Epidural Fentanyl", Anesthesia, vol. 37 (1982) pp. 309–316.

SCRIP No. 1276, Jan. 22, 1988, p. 17.

D. A. W. Bucks, "Skin Structure and Metabolism: Relevance to the Design of Cutaneous Therapeutics", Pharmaceutical Research (1984) pp. 148–153.

R. H. Guy, et al., "Transdermal Drug Delivery and Cutantous Metabolism", Xenobiotica, vol. 17, No. 3 (1987), pp. 325–343.

J. Kao, et al., "Skin Absorption and Cutaneous First Pass Metabolism of Topical Steroids: In Vitro Studies with Mouse Skin in Organ Culture".

C. Prottey, "The Molecular Basis of Skin Irritation", Cosmetic Science, vol. 1, Edited by M. M. Breuer, Academic Press (1978), pp. 275–348.

R. Saucedo, et al., "Morphine-Induced Skin Wheals: A Possible Model for the Study of Histamine Release", Clin. Pharmacol. Ther., vol. 38, No. 4 (1985), pp. 365–370.

S. S. M. Wang, et al., "Suppressive Effects of Oral Ketotifen on Skin Responses to Histamine, Codeine, and Allergen Skin Tests", Annals of Allergy, Vol. 55 (1985), pp. 57–60.

"The Dawn of Transdermal Man." Cyrus Technical Bulletin.

C. J. H. Andrews, et al., "Ventilatory Effects During and After Continuous Infusion of Fentanyl or Alfentanil", Br. J. Anaesth., Vol. 55 (1983), pp. 211S–216S.

G. Stuttgen, "Skin and Nail Penetration", Pharmacol. Skin., Vol. 1 (1987), pp. 22–40.

V. M. Knepp, et al., "Transdermal Drug Delivery: Problems and Possibilities", CRC Critical Reviews in Therapeutic Drug Carrier Systems (1987), pp. 13–37.

B. Kay, "Postoperative Pain Relief", Anaesthesia, Vol. 36 (1981), pp. 949–951.

E. A. Welchew, "On-Demand Analgesia", Anaesthesia, Vol. 38 (1983), pp. 19–25.

H. Rosenberg, et al., "Comparison of Intramuscular Analgesia, Intercostal Block, Epidural Morphine and On-Demand-I.V.-Fentanyl in the Control of Pain After Upper Abdominal Surgery", Anaesthesiol. Scand., Vol. 28 (1984), pp. 603–607.

C. Nieboer, et al., "The Effect of Occlusion of the Skin With Transdermal Therapeutic System on Langerhans' Cells and the Induction of Skin Irritation".

L.E. Mather, "Clinical Pharmacokinetics of Fentanyl and its Newer Derivatives", Clinical Pharmacokinetics, Vol. 8 (1983), pp. 422–446.

C. H. Hull, et al., "Control of Postoperative Pain by Interactive Demand Analgesia", Br. J. Anaesth. Vol. 43, No. 4 (1981), pp. 385–391.

R. J. Pohl, et al., "Cytochrome P–450 Content and Mixed-Function Oxidase Activity in Microsomes Isolated From Mouse Skin", Drug Metabolism and Disposition, Vol. 4, No. 5 (1976), pp. 442–450.

A. H. Ghamen, et al., "Mechanism of Action of Ethanol in Enhancing the Transport of Estradiol and Other Permeants in Hairless Mouse Skin", Pharmaceutical Research, Vol. 3, No. 5, Item 68 (October 1986 Supp.). Interactions, The University of Michigan College of Pharmacy, Winter 1986/87, p. 15.

S. Ahmad, "The Functional Roles of Cytochrome P–450 Mediated Systems: Present Knowledge and Future Areas of Investigations", Drug Metabolism Reviews, Vol. 10, No. 1 (1979), pp. 1–14.

G. Goerz, et al., "Animal Models for Cutaneous Drug-Metabolizing Enzymes", Models Dermatol. Vol. 3 (1987), pp. 93–105.

D. R. Bickers, et al., "Epidermis: A Site of Drug Metabolism in Neonatal Rat Skin", Pharmacology, Vol. 21 (1982), pp. 239–247.

D. M. Philbin, et al., "Histamine Release with Intravenous Narcotics: Protective Effects of $H_1$ and $H_2$-Receptor Antagonists", Klin. Wochenschr, Vol. 60 (1982), pp. 1056–1059.

J. M. Hermens, et al., "Comparison of Histamine Release in Human Skin Mast Cells Induced by Morphine, Fentanyl, and Oxymorphone", Anesthesiology, Vol. 62 (1985), pp. 124–129.

Casarett and Doull's Toxicology, Third Edition, MacMillan Publishing Company (1986), p. 68.

J. S. Finch, et al., "Clinical Investigation of the Analgesic Potency and Respiratory Depressant Activity of Fentanyl, a New Narcotic Analgesic", The Journal of Clinical Pharmacology (Jan.–Feb. 1967), pp. 46–51.

N. Grosman, "Histamine Release from Human Basophils and Isolated Rat Mast Cells Induced by Ketobemidone, Pethidine and the Spasmolytic A29", Acta pharmacol. et toxicol., Vol. 50 (1982), pp. 78–80.

T. B. Casale, et al., "Induction of Human Cutaneous Mast Cell Degranulation by Opiates and Endogenous Opioid Peptides: Evidence for Opiate and Nonopiate Receptor Participation", J. Allergy Clin. Immunol., Vol. 73, No. 6 (1983), pp. 775–781.

C. Prottey, "The Molecular Basis of Skin Irritation", Cosmetic Science, Vol. 1, Edited by M. M. Breuer, Academic Press (1978), pp. 275–348.

R. Saucedo, et al., "Morphine-Induced Skin Wheals: A Possible Model for the Study of Histamine Release", Clin. Pharmacol. Ther., Vol. 38, No. 4 (1985), pp. 365–370.

S. S. M. Wang, et al., "Suppressive Effects of Oral Ketotifen on Skin Responses to Histamine, Codeine, and Allergen Skin Tests", Annals of Allergy, Vol. 55 (1985), pp. 57-60.

A. S. Michaels, S. K. Chandrasekaran & J. E. Shaw, *Drug Permeation Through Human Skin: Theory and in Vitro Experimental Measurement*, September 1975, AIChE Journal, Volume 21, Number 5, Pages 985-996.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 16-39:

When transdermal systems, according to this invention, are applied to the skin, the drug will be transferred from the system into the skin where it is absorbed into the bloodstream to produce its systemic analgetic effect. We have found that skin contains fentanyl binding sites which must be saturated before any significant absorption into the bloodstream occurs. The variation from individual to individual and site to site appears to lie in the range of about 25-75 $\mu g/cm^2$ of the base [formed] *form of* fentanyl or its derivatives and the initial saturation of these sites should proceed rapidly in order to provide rapid onset of analgesia. Since most transdermal therapeutic systems exhibit an initial transitory, increased release of drug which occurs at a significantly higher rate than the steady-state rate later obtained, inclusion of additional amounts of the drug at the skin contacting surface of the device is not an absolute requirement. The systems described herein are capable of [delivery] *delivering* drug at initial rates which should induce the onset of analgesia within from two to four house after application but drug can be added to the adhesive layer or other skin contacting layer to more rapidly saturate the binding sites, if desired.

Column 4, lines 40-56:

The skin binding sites are also significant in establishing an upper limit on the size of the transdermal therapeutic system and, conversely, the lower limit on the usable delivery rate. The total amount of drug contained in the binding sites is directly proportional to the surface area of the delivery system [and is independent of the rate at which the drug is delivered]. When a maximum sized, 100 cm$^2$ system according to this invention is employed, the total amount of drug within the binding sites could be from at least 2.5 to 7.5 mg. When such a system is removed the total amount of bound drug must be absorbed by the body before the action of the drug stops. In view of the high potency of fentanyl and its derivatives, it is preferable that the amount of drug solubilized in the skin be maintained at or below *the* 3.75 mg level to permit prompt termination of therapy.

Column 7, lines 3-16:

Specific examples of various transdermal therapeutic systems according to our invention which are capable of administering fentanyl at the desired rates for extended periods of time will be described in the examples set [for] *forth* hereinafter. However, in order for the residual drug in depleted systems to be minimized [we have discovered that], the initial concentration of the fentanyl in the matrix material should be [selected such that it is less than 0.5 0.5 mg/cm$^2$. For this reason the] *minimized. We have discovered that with* aqueous-ethanol [reservoir] *reservoirs* [systems which permit], unit activity *of the drug* [to be achieved at this low concentration] *may be attained in the reservoir at initial fentanyl loadings of about 0.5 mg/cm$^2$ or less and for this reason the aqueous-ethanol reservoir systems* are presently considered preferable according to our invention. In the following examples all percentages are by weight unless noted.

Column 7, lines 19-68:

Transdermal therapeutic systems according to FIG. 1 utilizing an aqueous ethanolic gel reservoir were prepared in 10, 20 and 40 cm$^2$ sizes. Fentanyl base was added to 95% ethanol and stirred to dissolve the drug. Purified water was added to the ethanol-fentanyl solution in amounts sufficient to generate a mixture containing 14.7 mg/g of fentanyl in a 30% ethanol-water solvent. Two percent of hydroxyethyl cellulose gelling agent was added to this solution slowly with stirring and mixed until a smooth gel was obtained (approximately one hour). A 0.05 mm thick contact adhesive layer was formed on a fluorocarbon-diacrylate treated polyester film which comprised the release liner for the system by solution casting an amine resistant silicone medical adhesive onto the polyester film from a solution in [trichlorotrifloroethane] *trichlorotrifluoroethane*. A 0.05 mm thick rate controlling membrane comprised of EVA (9VA) was pressure laminated to the exposed adhesive. A backing member comprised of a multilaminate of polyethylene, aluminum, polyester and EVA was also provided and the aqueous gel pouched between the backing member and the release linear adhesive/rate controlling membrane on a rotary heat-seal machine at a gel loading of 15 mg/cm$^2$. Sealed pouches in the sizes of 10, 20 and 49 cm$^2$ were die cut and immediately pouched to avoid loss of ethanol. The pouched systems were allowed to equilibrate for at [last] *least* two weeks in order to reach equilibrium concentration of the drug and ethanol in the rate controlling and adhesive layers. After this time the drug reservoir no longer contained any excess drug and the drug concentration in the reservoir had reduced to 8.8 mg/g, the saturation concentration of fentanyl in 30% ethanol. The in vitro fentany flux through cadaver skin into an infinite aqueous sink at 32° C. was measured and is shown in FIG. 4. As can be seen the fentanyl flux rapidly increased to approximately 1.35 $\mu g/cm^2/hr$ in slightly more than four hours and remained substantially constant thereafter. The saturation of the drug in skin occurred during the time the drug flux was increasing to its steady state value. After operation for approximately 24 hours substantially all of the ethanol will have been delivered and the transport rate of fentanyl through skin will have been reduced to the level obtained when no ethanol is present. It would be desirable that the use of this system be discontinued at that point. The systems originally contained approximately 200 $\mu g/cm^2$ of fentanyl and over the 24 hour useful life delivered approximately 50 $\mu g/cm^2$ resulting in a delivery of approximately 25% of the original drug loading.

Column 8, line 40 - Column 9, line 6:

A multilaminate transdermal therapeutic [systems] *system* of the type described with respect to FIG. 2 was prepared by adding low molecular weight polyisobutylene [PIB] (*PIB*) (average molecular weight of 35,000) and high molecular weight PIB (average molecular weight 1,200,000) to a stirring [a] ratio of 1.25 to 1. Light mineral oil (MO) [as] *was* added to the same vessel with a ratio of approximately 1.125 to 1 part of [(PIB)] *PIB*. Heptane was added and the mixture was stirred until the polymers dissolved. Sufficient fentanyl base was added to the solution to generate a blend of 20 percent fentanyl in the PIB/MO. The polymer-drug blend was solvent cast onto an occlusive backing such as described in Example 1 and allowed to evaporate to form [approximate 0.05 mm thick] *a drug reservoir approximately 0.05 mm thick*. Microporous [polypropelene] *polypropylene film saturated with mineral oil was pressure laminated to the reservoir layer. A PIB/MO mixture was described above but containing sufficient additional fentanyl to provide a* 2 percent loading of fentanyl as undissolved solid was cast in a layer approximately 0.05 mm thick on a siliconized polyester release liner film and the thus formed composite laminates were laminated together to form a device as shown in FIG. 3. Individual systems were die cut from this laminated film in the sizes of 2.5, 5, 10 and 20 cm² circles and were packaged. The in vitro fentanyl flux from the systems produced according to this [examples] *example* through cadaver skin at 32° C. into an infinite sink are shown in FIG. 6. Samples differing from those described above by having a solid drug loading of 3.2% were also fabricated. As can be seen from FIG. 6, 2% solid drug was adequate to produce a rapid onset of therapy without an unnecessarily high initial drug release rate and after the initial transitory period both systems provided a steady release rate of approximately 1.8 μg/cm²hr for up to 70 hours.

Column 9, lines 9-22:

A monolithic [systems] *system* according to FIG. 3 was fabricated by preparing a PIB/MO fentanyl base mixture as set forth in Example 4 which was solvent cast onto an occlusive backing and after evaporation of the solvent, laminated to the siliconized release liner. The PIB matrices were fabricated at 10, 20 and 30 percent fentanyl loading and drug transport rates from such systems through human cadaver skin at 32° C. into an infinite sink were measured. The results are shown in FIG. 7. The systems showed the typical time dependent drug release rates from a monolith; however, continued delivery at [a] relatively constant rates through skin for up to 80 hours within the ranges required according to this invention were obtained.

AS A RESULT OF REEXAMINATION, IT HAS BEEN DETERMINED THAT:

Claims 1-7, 9, 16, 22-29, 31, 32, 34-38, 40, 41, 44, 47 and 49-58 are determined to be patentable as amended.

Claims 8, 10-15, 17-21, 30, 33, 39, 42, 43, 45, 46 and 48, dependent on an amended claim, arre determined to be patentable.

New claims 59-110 are added and determined to be patentable.

1. A process for inducing and maintaining analgesia *in a human being by the transdermal administration of a material selected from the group consisting of fentanyl and its analgetically effective derivatives* which comprises *transdermally* administering *to said human being* through an area of intact skin, a skin permeable form of [a] said material [selected from the group consisting of fentanyl and its analgetically effective derivatives] at an analgetically effective rate and continuing the administration of said material *to said human being* at said rate for an extended period of time at 'east sufficient to induce analgesia.

2. The process of claim 1, *3, 4, 5, 6, 7, 8, 9, 10, 11, 12, 13, 14, 15, 16, 17, 18, 19, 21, 100 or 105* further comprising the coadministration with said material of a skin permeation enhancer for said material.

3. [The process of claim 1] *A process for inducing and maintaining analgesia in a human being by the transdermal administration of a material selected from the group consisting of fentanyl and its analgetically effective derivatives which comprises transdermally administering to said human being through an area of intact skin, a skin permeable form of said material at an analgetically effective rate and continuing the administration of said material to said human being at said rate for an extended period of time at least sufficient to induce analgesia wherein said extended period of time is in the range of about 24 hours to 7 days.*

4. [The process of claim 1] *A process for inducing and maintaining analgesia in a human being by the transdermal administration of a material selected from the group consisting of fentanyl and its analgetically effective derivatives which comprises transdermally administering to said human being through an area of intact skin, a skin permeable form of said material at an analgetically effective rate and continuing the administration of said material to said human being at said rate for an extended period of time at least sufficient to induce analgesia* wherein the steady state administration rate of said material is maintained within the range of about 10 to 300 μg/hr for a substantial portion of said extended period of time.

5. [The process of claim 1] *A process for inducing and maintaining analgesia in a human being by the transdermal administration of a material selected from the group consisting of fentanyl and its analgetically effective derivatives which comprises transdermally administering to said human being through an area of intact skin, a skin permeable form of said material at an analgetically effective rate and continuing the administration of said material to said human being at said rate for an extended period of time at least sufficient to induce analgesia* wherein said area of intact skin is within the range of about 5 to 100 cm² and said material is delivered through the skin at a flux within the range of about 0.5 to 10 μg/cm²/hr.

6. The process of claim 5 in which said area is in the range of about 10-50 cm² and said [rate] *flux* is in the range of about 1-5 μg/cm²/hr.

7. The process of claim 4 wherein the steady state administration rate is in the range of about 25 to 150 μg/hr.

9. The process of claim 1 wherein said material is the base form of a material selected from the group consisting of fentanyl, [sufentanyl] *sufentanil*, [carfentanyl] *carfentanil*, [lofentanyl] *lofentanil*, and [alfentanyl] *alfentanil*.

16. A process for *inducing and maintaining analgesia in a human being by* the transdermal administration *to a human being* of a material selected from the group consisting of fentanyl and its analgetically effective derivatives which comprises:

(a) contacting a predetermined area of the intact skin *on said human being* with a source of a skin permeable form of said material;

(b) maintaining said source in material transmitting relationship to said area of intact skin for an administration period sufficient to induce analgesia of at least about [12] *24* hours; and (c) delivering said material into [the] *said skin at a* [rate] *flux* within the range of about [0.1-10] *0.5-10 µg/cm²/hr* [for at least about 12 hours] *substantially throughout said administration period.*

22. A medical device for *inducing and maintaining analgesia in a human being by* the transdermal administration *to a human being* of a material selected from the group consisting of fentanyl and its analgetically effective derivatives at an analgetically effective rate for an extended period of time of at least about [four] *24 hours and sufficient to induce and maintain analgesia* which comprises:

(a) reservoir means containing a skin permeable form of said said administration period *material in an amount sufficient to deliver said material at said analgetically effective rate for said extended period of time; and*

(b) means for maintaining said reservoir means in material transmitting relationship to the intact skin on said human being.

23. [The medical device of claim 22] *A medical device for the transdermal administration of a material selected from the group consisting of fentanyl and its analgetically effective derivatives to a human being at an analgetically effective rate for an extended period of time of at least about* 24 hours and sufficient to induce and maintain analgesia which comprises:

(a) *reservoir means containing a skin permeable form of said material in an amount sufficient to deliver said material at said analgetically effective rate for said extended period of time; and*

(b) *means for maintaining said reservoir means in material transmitting relationship to the intact skin on said human being* wherein said [system] *device* delivers the base form of the material through intact skin at a rate in the range of from about 10 to 300 µg/hr for a substantial portion of said period of time.

24. The medical device of claim 22, 23, 25, 26, 27, *101 or 106* wherein said reservoir means contains a skin permeation enhancer for said material.

25. [The medical device of claim 22] *A medical device for the transdermal administration to a human being of a material selected from the group consisting of fentanyl and its analgetically effective derivatives at an analgetically effective rate for an extended period of time of at least about 24 hours and sufficient to induce and maintain analgesia which comprises:*

(a) *reservoir means containing a skin permeable form of said material in an amount sufficient to deliver said material at said analgetically effective rate for said extended period of time; and*

(b) means for maintaining said reservoir means in material transmitting relationship to an area of intact skin on said human being wherein said [predetermined] area is in the range of about 5-100 cm² and the [rate of delivery of] *device delivers* said material [is in] *through the skin of said human being at a flux within* the range of about 0.5-10 µg/cm²/hr.

26. The medical device of claim 25 wherein said area is in the range of about 10-50 cm² and the [rate of delivery] *flux* is in the range of about 1-5 µg/cm²hr.

27. The medical device of claim 22, *23, 24 or 25* wherein said material is fentanyl base.

28. A medical device for *inducing and maintaining analgesia in a human being by the* continuous transdermal administration *to a human being* of a material selected from the group consisting of fentyl and its analgetically effective [derivates] *derivatives at an analgetically effective administration rate and duration* comprising, in combination:

(a) a reservoir for said material having a skin proximal, material releasing surface area in the range of about 5-100 cm², said reservoir containing between 0.1 and 50% by weight of a skin-permeable form of said material in amounts and at a concentraton adequate to permit delivery of said material through the intact [human] *of said human being* at a [rate] flux within the range of from 0.5 to 10 µg/cm²/hr for at least about [12] *24* hours; and (b) means for maintaining said reservoir in material transmitting to said skin.

29. The medical device of claim 28 wherein said means for maintaining said reservoir in material transmitting relationship to the skin is an amine resistant *silicone* adhesive disped in the flow path of the material from the reservoir to the skin.

31. The medical device of claim [17] *28* wherein said material is the base form of a material selected from the group consisting of fentanyl, [sufentanyl], *sufentanil*, [carfentanyl], *carfentanil*, [lofentanyl] *lofentanil* and [alfentanyl] *alfentanil.*

32. The medical device of claim [17] *28* reservoir contains an aqueous gel comprising up to about 47% [of 95%] ethanol *on a 95% ethanol basis,* 1-10% gelling agent, 0.1-10% of said material, and release rate controlling means disposed between said reservoir and the skin, said release rate controlling means being less permeable to said material than to ethanol.

34. The medical device of claim 30 further comprising permeation enhancer means for increasing the permeability of said material of the skin to which said device is applied.

35. The medical device of claim 34 wherein said permeation enhancer means is admixed in said reservoir means.

36. The medical device [system] of claim 35 [wherein said] *further comprising release rate controlling means which* restricts the flux of said material from said [system] *device* substantially more than the flux of said permeation enhancer from said device.

37. The medical device of claim 30 wherein said reservoir is an aqueous gel comprising approximately from 0-47% of [95%] ethanol *on a 95% ethanol basis,* 1-10% gelling agent, *and* 0.1-10% of said material.

38. The medical device of claim 37 wherein said aqueous gel comprises from approximately 20-35% of said ethanol *on a 95% ethanol basis,* 1-5% gelling agent and 0.1-2% of said material.

40. The medical device of claim 39 wherein said material is initially contained in said reservoir at equilibrated levels no greater than 0.5 [µg] *mg/cm².*

41. The medical device of claim 39 wherein said means for maintaining said system on the skin is an amine resistant *silicone* adhesive disposed on said release rate controlling means and said material is fentanyl.

44. The medical device of claim 43 wherein said means for maintaining said device in material transmitting relationship to the skin is an amine resistant *silicone* adhesive disposed in the flow path of the material from the reservoir to the skin.

47. The medical device of claim 46 in which said means for maintaining said device in material transmitting relationship to the skin is an amine resistant *silicone* adhesive disposed on said release rate controlling means.

49. The medical device of claim 28 wherein said [release rate] *flux* is in the range of from about 1-5 µg/cm$^2$/hr and said material is fentanyl *base*.

50. The medical device of claim 30 wherein said [release rate] *flux* is in the range of from about 1-5 µg/cm$^2$/hr and said material is fentanyl *base*.

51. The medical device of claim 35 wherein said release rate] *flux* is in the range of from about 1-5 µg/cm$^2$/hr and said material is fentanyl base.

52. The medical device of claim 36 wherein said [release rate] *flux* is in the range of from about 1-5 µg/cm$^2$/hr and said material is fentanyl *base*.

53. The medical device of claim 38 wherein said [release rate] *flux* is in the range of from about 1-5 µg/cm$^2$/hr and said material is fentanyl *base*.

54. The medical device of claim 40 wherein said [release rate] *flux* is in the range of from about 1-5 µg/cm$^2$/hr and said material is fentanyl *base*.

55. The medical device of claim 43 wherein said [release rate] *flux* is in the range of from about 1-5 µg/cm$^2$/hr and said material is fentanyl *base*.

56. The medical device of claim 44 wherein said [release rate] *flux* is in the range of from about 1-5 µg/cm$^2$/hr and said material is fentanyl *base*.

57. The medical device of claim 45 wherein said [release rate] *flux is in the range of from about* 1-5 µg/cm$^2$/hr and said material is fentanyl *base*.

58. The medical device of claim 47 wherein said [release rate] *flux* is in the range of from about 1-5 µg/cm$^2$/hr and said material is fentanyl *base*.

59. *The process of claim 1, 3, 4, 5, 6, 7, 8, 9, 10, 11, 12, 13, 14, 15, 16, 17, 18, 19, 20, 21, 100 or 105 wherein said extended period of time is at least about 3 days.*

60. *The device of claim 22, 23, 25, 26, 27, 101, or 106 wherein said extended period of time is at least about 3 days.*

* * * * *

REEXAMINATION CERTIFICATE (3730th)

United States Patent
[11] B2 4,588,580

Gale et al.
[45] Certificate Issued Feb. 16, 1999

[54] TRANSDERMAL ADMINISTRATION OF FENTANYL AND DEVICE THEREFOR

[75] Inventors: Robert M. Gale, Los Altos; Victor Goetz, Palo Alto; Eun S. Lee, Redwood City; Lina T. Taskovich, Palo Alto; Su I. Yum, Los Altos, all of Calif.

[73] Assignee: Alza Corporation, Palo Alto, Calif.

Reexamination Request:
No. 90/004,965, Apr. 14, 1998

Reexamination Certificate for:
Patent No.: 4,588,580
Issued: May 13, 1986
Appl. No.: 633,762
Filed: Jul. 23, 1984

Reexamination Certificate B1 4,588,580 issued Jan. 3, 1989

Certificate of Correction issued Aug. 22, 1989.

[51] Int. Cl.$^6$ .............. A01N 25/04; A61K 9/70
[52] U.S. Cl. .............. 424/21; 424/14; 424/16; 424/19; 424/22; 514/316; 514/329; 604/896; 604/897; 604/93; 604/304; 604/307

[58] Field of Search ............... 424/21, 14, 16, 424/19, 22; 514/316, 329; 604/896, 897, 93, 304, 307

[56] References Cited

U.S. PATENT DOCUMENTS

| | | | |
|---|---|---|---|
| 4,466,953 | 8/1984 | Keith et al. | 424/28 |
| 4,470,962 | 9/1984 | Keith et al. | 424/28 |

FOREIGN PATENT DOCUMENTS

| | | |
|---|---|---|
| 040861 | 12/1981 | European Pat. Off. |
| 142210 | 5/1996 | Japan |

*Primary Examiner*—Nathan M. Nutter

[57] ABSTRACT

Transdermal delivery systems for delivery of fentanyl and its analgetically effective derivatives for extended periods of time are disclosed which deliver the base form of the drug at a rate of from 0.5 to 10 µg/cm$^2$/hr for a substantial portion of their useful life. The systems can be from 5–100 cm$^2$ in releasing surface and preferably employ an in-line amine resistant adhesive. Preferred rate controlled systems utilize an aqueous ethanolic gel to minimize drug content.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–110 is confirmed.

* * * * *